United States Patent
Kaesemeyer

(10) Patent No.: US 8,936,635 B2
(45) Date of Patent: Jan. 20, 2015

(54) BIORESORBABLE NITRIC OXIDE AGONIST PRODRUG SCAFFOLDS FOR VASCULAR STENTS

(75) Inventor: Wayne H Kaesemeyer, Chapel Hill, NC (US)

(73) Assignee: Palmetto Pharmaceuticals LLC, Charleston, SC (US)

( * ) Notice: Subject to any disclaimer, the term of this patent is extended or adjusted under 35 U.S.C. 154(b) by 214 days.

(21) Appl. No.: 13/426,948

(22) Filed: Mar. 22, 2012

(65) Prior Publication Data
US 2012/0245677 A1 Sep. 27, 2012

Related U.S. Application Data

(60) Provisional application No. 61/457,419, filed on Mar. 23, 2011.

(51) Int. Cl.
*A61F 2/06* (2013.01)
*A61L 31/14* (2006.01)
*A61L 31/16* (2006.01)

(52) U.S. Cl.
CPC .............. *A61L 31/148* (2013.01); *A61L 31/16* (2013.01); *A61L 2300/422* (2013.01); *A61L 2300/434* (2013.01)
USPC ........................................ 623/1.38; 623/1.42

(58) Field of Classification Search
CPC ................ A61F 2250/0067; A61F 2210/0004; A61F 2310/0097
USPC ..................... 623/1.38, 1.42–1.46, 1.49, 1.13
See application file for complete search history.

(56) References Cited

U.S. PATENT DOCUMENTS

| | | | |
|---|---|---|---|
| 4,265,247 A | 5/1981 | Lenz et al. | |
| 5,085,629 A | 2/1992 | Goldberg | |
| 5,744,153 A | 4/1998 | Yewey et al. | |
| 5,767,160 A | 6/1998 | Kaesemeyer | |
| 6,425,881 B1 | 7/2002 | Kaesemeyer | |
| 6,623,521 B2 | 9/2003 | Steinke et al. | |
| 2004/0142902 A1 | 7/2004 | Struijker-Boudier | |
| 2008/0194614 A1 | 8/2008 | Dorent et al. | |
| 2008/0249608 A1 | 10/2008 | Dave | |
| 2009/0306120 A1 | 12/2009 | Lim et al. | |
| 2011/0105996 A1 | 5/2011 | Mustooe et al. | |
| 2013/0095160 A1 | 4/2013 | Ghatnekar et al. | |

FOREIGN PATENT DOCUMENTS

WO WO 2004/105737 12/2004

OTHER PUBLICATIONS

Nomura et al "Ring-opening polymerization of lactones by rare-earth metal triflates and by their reusable system in ionic liquids" Tetrahedron, 2007; 63, 8478-8484.

Whang et al., J. Biomedical Materials Research, 2005 74A: 237-247.
Krinick et al., Makromolecular Chemistry 1990 191:839-856 Abstract.
Office Action, dated Apr. 24, 2013 in U.S. Appl. No. 13/612,054.
Albertsson et al., Biomacromolecules, vol. 4, No. 6, pp. 1466-1486 (2003).
Kaesemeyer et al., "Bioresorbable Polystatin Fourth-Generation Stents" Coron Artery Dis, vol. 24(6), pp. 516-521 (2013).
Kaesemeyer, "Statin DES for Early Stent Thrombosis," Atherosclerosis. 207: 343 (2009).
Long et al., "FK506 Binding Protein 12/12.6 Depletion Increases Endothelial NO Synthase Threonine 495 Phosphorylation and blood Pressure," Hypertension, 49: 569-76 (2007).
Capodanno et al., "Novel Drug-eluting Stents in the Treatment of de novo Coronary Lesions", Vascular Health and Risk Management, vol. 7, pp. 103-118 (2011).
Krishnan, "Simvastatin Incorporated Perivascular Polymeric Controlled Drug Delivery System for the Inhibition of Vascular Wall Intimal Hyperplasia," A Thesis Presented to The Graduate Faculty at The University of Akron. Aug. 2007.
Rashidi et al., "Simvastatin Release from Poly(lactide-co-glycolide) Membrane Scaffolds," Polymers, vol. 2, pp. 709-718 (2010).
Benoit et al., "Synthesis and Characterization of a Fluvastatin-Releasing Hyrogel Delivery System to Modulate hMSC Differentiation and Function for Bone Regeneration." Biomaterials, 27: 6102-10 (2006).
Jaschke et al., "Local Statin Therapy Differentially Interferes with Smooth Muscle and Endothelial Proliferation and Reduces Neointima on a Drug-Eluting Stent Platform," Cardiovas Res, 68: 483-92(2005).
Miyauchi et al., "Effectiveness of Statin-Eluting Stent on Early Inflammatory Response and Neointimal Thickness in a Porcine Coronary Model," Circ J. 72: 832-8 (2008).
Mehran et al. "Impact of Bleeding on Mortality After Percutaneous Coronary Intervention" JACC Cardiovasc Interv. 2011; 4(6):654-64.
Pendyala et al., "The First-Generation Drug Eluting Stents and Endothelial Dysfunction," J. Am Coll Cardiol Intv, 2: 1169-77 (2009).
Nomura et al "Ring-opening polymerization of lactones by rare-earth metal triflates and by their reusable system in ionic liquids" Tetrahedron, 2007; 63, 8478-7.

(Continued)

Primary Examiner — Howie Matthews

(57) ABSTRACT

The present invention relates to a bioresorbable scaffold for a vascular stent comprising a nitric oxide agonist and a polymer comprising a lactide, a glycolide and a lactone. The nitric oxide agonist is a statin or a HMG CoA reductase inhibitor. The nitric oxide agonist may be coated on the polymer, incorporated within the polymer or chemically bonded to the polymer. The invention also relates to a method for treating atherothrombosclerotic occlusive disease of an artery comprising implanting into the artery a stent with a bioresorbable scaffold comprising a nitric oxide agonist and a polymer comprising a lactide, a glycolide and a lactone, wherein the nitric oxide agonist is exuded from or released from the bioresorbable scaffold.

27 Claims, No Drawings

(56) References Cited

OTHER PUBLICATIONS

Moller et al, Abstract Stannous(II) Trifluoromethane Sulfonate: A Versatile Catalyst for the Controlled Ring-Opening Polymerization of Lactides: Formation of Stereoregular Surfaces from Polylactide "Brushes". J. Polym. Sci. A.,2001; 39, 3529-3538.
Kaesemeyer et al., "Pravastatin Sodium Activates Endothelial Nitric Oxide Synthase Independent of its Cholesterol Lowering Actions," J. Am. Coll. Cardiol. 33:234-41 (1999).
Datar et al., "Acute Activation of eNOS by Statins Involves Scavenger Receptor-B1, G-Protein Subunit Gi Phospholipase C and Calcmium influx" Br J Pharmacol. 160: 1765-72 (2010).
Luscher et al "Drug-Eluting Stent and Coronary Thrombosis : Biological Mechanisms and Clinical Implications" Circulation (2007) 115:1051-58.
Valente et al "STEMI patients—the more you bleed, the more you die: a comparison between classifications." Clin Cardiol. 2011; 34(2):90-6.
Onuma et al. "Bioresorbable scaffold: the advent of a new era in percutaneous coronary and peripheral revascularization?" Circulation. 201; 123(7):779-97, 2011.
Pektok et al. "Degradation and Healing Characteristics of Small-Diameter Poly(Epsilon-Caprolactone) Vascular Grafts in the Rat Systemic Arterial Circulation" Circulation (2008) 118:2563-2570.
Alfonso et al. "Second-generation drug-eluting stents moving the field forward". J Am Coll Cardiol. 2011; 58(1):26-9.
Balakrishnan et al "Intravascular Drug Release Kinetics Dictate Arterial Drug Deposition, Retention, and Distribution" J Control Release. 2007; 123(2):100-8.
Kolachalama "Luminal flow patterns dictate arterial drug deposition in stent based delivery". J Control Release. 2009; 133(1):24-30.

BIORESORBABLE NITRIC OXIDE AGONIST PRODRUG SCAFFOLDS FOR VASCULAR STENTS

The present application claims benefit under 35 U.S.C. 119(e) of Provisional Application No. 61/457,419, filed Mar. 23, 2011, the disclosure of which is expressly incorporated by reference herein in its entirely.

FIELD OF THE INVENTION

Bioresorbable nitric oxide agonist prodrug scaffolds for vascular stents are disclosed. Principal among these are scaffolds formed from polystatin polymers. These scaffolds can have intrinsic pharmacologic bioactivity. According to embodiments of the invention, they can accomplish one or more of the following: increase nitric oxide, prevent endothelial dysfunction induced by antirestenosis agents used in drug eluting stents, promote re-endothelization, reduce the risk of stent thrombosis and the requirement for antiplatelet drug therapy and its risk of bleeding, and related morbidity and mortality, following procedure related vascular lumen injury.

BACKGROUND OF THE INVENTION

Vascular stent construction begins with a scaffold, a spring-like device which props open the lumen of an artery or vein following the performance of a procedure, such as an angioplasty, which is done to open a vessel narrowed by a disease such as atherosclerosis, without or with accompanying thrombosis. Thus far vascular stent construction has mainly involved scaffolds with metallic compositions. This has led to a first generation bare metal stent involving a scaffold only which has been followed by a second generation stent which elutes drugs for preventing restenosis. Drugs have either been directly applied to the scaffold of these stents or eluted from polymers coated onto the metallic scaffolds of stents. Drug eluting stents have largely solved the problem of restenosis; however, the drugs used, paclitaxel and mTOR or cell cycle inhibitors such as rapamicin, sirolimus, etc., have done this at the cost of causing endothelial dysfunction, impaired re-endothelization and stent thrombosis See Long et al., "FK506 Binding Protein 12/12.6 Depletion Increases Endothelial Nitric Oxide Synthase Threonine 495 Phosphorylation and Blood Pressure," Hypertension, 49: 569-76 (2007); and Pendyala et al., "The First-Generation Drug Eluting Stents and Endothelial Dysfunction," J. Am Coll Cardiol Intv, 2: 1169-77 (2009). This has led to a prolonged requirement for dual antiplatelet therapy with its inherent risk of bleeding.

Regarding antiplatelet therapy, current guidelines recommend 12 or more months of dual antiplatelet therapy following placement of a drug eluting stent. There currently is a need in the art for this period to be reduced to 3 months or less in order to reduce the risk of bleeding from prolonged antiplatelet drug therapy.

Recently a stent scaffold has been constructed from a polylactide polymer typically used to make bioresorbable sutures and other related bioresorbable surgical devices. See Capodanno et al., "Novel Drug-eluting Stents in the Treatment of de novo Coronary Lesions", Vascular Health and Risk Management, vol. 7, pp 103-118 (2011). This scaffold has been used to fabricate a stent which elutes everolimus, an antirestenosis agent, from a biodegradeable polymer coated on the surface of the scaffold. This discovery has led to the development of a third generation stent which passively disappears from the vessel lumen over a period of one to two years and is thought to reduce the risk of stent thrombosis. However, the effect of this stent on the risk of stent thrombosis is currently unknown and under investigation in clinical trials. The bioresorbable vascular scaffold in this stent, unlike the scaffolds of the present invention, has no intrinsic pharmacologic biological activity.

Polylactide is a terpolymer of (a) L(−)lactide, (b) glycolide, and (c) epsilon-caprolactone. The L(−) lactide component varies from 45-85% by weight. Glycolide varies from 5-50% by weight. And the epsilon-caprolactone varies from about 15 to 25% by weight. The initial use of polylactide in bioresorbable stent construction was for urethral stents. See Goldberg et al., U.S. Pat. No. 5,085,629.

The process of synthesizing polylactide involves the presence of a lactone ring in epsilon-caprolactone. HMG CoA reductase inhibitors, or statins, likewise have structures that can exist in a form with a closed lactone ring. It has recently been shown that a statin can be polymerized with DL-lactide-glycolide to form polystatin containing microspheres which can be placed in a PolyRing for sustained perivascular drug delivery to vascular grafts and dialysis access devices to prevent intimal hyperplasia. See Krishnan, "Simvastatin Incorporated Perivascular Polymeric Controlled Drug Delivery System for the Inhibition of Vascular Wall Intimal Hyperplasia," A Thesis Presented to The Graduate Faculty at The University of Akron. August, 2007. More recently, sustained simvastatin release from a poly(lactide-co-glycolide) membrane has been shown to have potential for use as a controlled release scaffold for bone tissue engineering. See Rashidi et al., "Simvastatin Release from Poly(lactide-co-glycolide) Membrane Scaffolds," Polymers, vol 2, pp 709-718 (2010). This study utilized methods of an earlier study. See Benoit et al., "Synthesis and Characterization of a Fluvastatin-Releasing Hyrogel Delivery System to Modulate hMSC Differentiation and Function for Bone Regeneration. Biomaterials," 27: 6102-10 (2006).

A bioresorbable polystatin for use in constructing scaffolds for vascular stents is attractive because with metabolism of the polystatin to its monomeric form which occurs in the bioresorption process, the action of the exuded statin to increase the activity of nitric oxide synthase is felt to reduce the risk of stent thrombosis and the need for post stent antiplatelet therapy with its risk of bleeding. See Kaesemeyer, "Statin DES for Early Stent Thrombosis," Atherosclerosis. 207: 343 (2009); Kaesemeyer, U.S. Pat. No. 6,425,881; Jaschke et al., "Local Statin Therapy Differentially Interferes with Smooth Muscle and Endothelial Proliferation and Reduces Neointima on a Drug-Eluting Stent Platform," Cardiovas Res, 68: 483-92(2005); and Miyauchi et al., "Effectiveness of Statin-Eluting Stent on Early Inflammatory Response and Neointimal Thickness in a Porcine Coronary Model," Circ J. 72: 832-8 (2008). The same principal applies to any nitric oxide agonist possessing a lactone ring in its structure that will permit polylactide polymer formation.

A bioabsorbable polymer scaffold for a stent is taught by Johnson et al., US published Application No. 2008/0249608. The scaffold comprises a plurality of hoop components configured as the primary radial load bearing elements of the intraluminal scaffold; and one or more connector elements interconnecting the plurality of hoop components, wherein at least one of the plurality of hoop components and the one or more connector elements comprises a composite structure formed from a bioabsorbable metallic material and a bioabsorbable polymeric material. Although Johnson describes a plurality of therapeutic and pharmaceutic agents including a statin which can be coated on the scaffold, the Johnson scaffold does not include a statin incorporated into the polylactide polymeric scaffold, as taught according to embodiments of the present invention. And upon bioresorpton of the Johnson et al scaffold, the added drugs can exert their separate pharmacologic bioactivities but, overall, the scaffold illustrates extrinsic pharmacologic bioactivity instead of the intrinsic pharmacologic bioactivity seen with the scaffold of the present invention. And this is because the Johnson scaffold, minus the effects of the drugs added to the scaffold, has no "intrinsic" pharmacologic activity and does not function as a prodrug during the process of bioresorption, as does the scaffold described herein. Lastly, unlike the Johnson scaffold, the pharmacologically active agents in the scaffold of this invention are chemically bonded as monomers in the overall polymeric structure of the bioresorbable scaffold.

Lim et al., US published Application No. 2009/0306120, discloses an amorphous terpolymer comprising a lactide, a glycolide and caprolactone, which can be a coating on an implantable device for controlling the release of drugs or can be a bioabsorabable implantable device such as a bioabsorbable stent. Lim et al. disclose lists of biologically active agents including lovastatin (a drug that inhibits HMG-CoA reductase). Lim et al. does not teach a scaffold comprising a L(-) lactide—glycolide-statin terpolymer according to embodiments of the present invention. And upon bioresorpton of the Lim et al scaffold, the added drugs can exert their separate pharmacologic bioactivities but, overall, the scaffold illustrates extrinsic pharmacologic bioactivity instead of the intrinsic pharmacologic bioactivity seen with the scaffold of the present invention. The Lim scaffold, minus the effects of the drugs added to the scaffold, has no "intrinsic" pharmacologic activity and does not function as a prodrug during the process of bioresorption, as does the scaffold described herein. Lastly, unlike the Lim scaffold, the pharmacologically active agents in the scaffold of this invention are chemically bonded as monomers in the overall polymeric srtucture of the bioresorbable scaffold.

SUMMARY OF THE INVENTION

The present invention adds intrinsic pharmacologic bioactivity to a bioresorbable scaffold used in the construction of vascular stents. The invention relates to a bioresorbable scaffold comprising a polylactide polymer of an agonist of nitric oxide, which functions as a prodrug to upregulate nitric oxide, prevent endothelial dysfunction and promote re-endothelialization to reduce the risk of stent thrombosis. The polylactide polymer can be a polystatin polylactide polymer. The present invention relates to the construction of a 4th generation vascular stent which has a drug exuding scaffold. The present invention relates to forming a stent which is both drug exuding and drug eluting that targets both stent thrombosis and restenosis. Embodiments of the present invention can be useful in reducing the risk of stent thrombosis, thus reducing the requirements for antiplatelet therapy. Also the risk of bleeding following stent placement may be markedly reduced.

In the present invention, the drug exuding scaffold may be used alone. In another aspect of the present invention, the drug exuding scaffold can be used in conjunction with drugs coated directly onto the scaffold. In yet another aspect of the present invention, the drug exuding scaffold can be used in conjunction with drugs placed in a polymer which is subsequently coated onto the scaffold's surface.

The present invention also relates to a bioresorbable scaffold for a vascular stent comprising a nitric oxide agonist and a polymer comprising a lactide, a glycolide and a lactone. The nitric oxide agonist may be a statin or HMG CoA reductase inhibitor. The statin may be selected from the group consisting of velostatin, dihydrocompactin, carvastatin, bevastatin, cefvastatin, glenvastatin, simvastatin, lovastatin, atorvastatin, pravastatin, cerivastatin, rosuvastatin, pitavastatin, fluvastatin, mevastatin, dalvastatin, compactin and mixtures thereof. The nitric oxide agonist, statin or HMG CoA reductase inhibitor may be coated on the polymer. The nitric oxide agonist, statin or HMG CoA reductase inhibitor may be incorporated within on the polymer or chemically bonded to the polymer.

The present invention also relates to a drug-eluting stent with the aforementioned bioresorbable scaffold.

The present invention also relates to a method for treating atherothrombosclerotic occlusive disease of an artery comprising implanting into the artery a stent with a bioresorbable scaffold comprising a nitric oxide agonist and a polymer comprising a lactide, a glycolide and a lactone, wherein the bioresorbable scaffold exudes the nitric oxide agonist. The nitric oxide agonist may be a statin and the artery may be a coronary, carotid, intracranial, aorta, renal, or peripheral artery.

The present invention also relates to a method for treating diseases of a vein comprising implanting into the vein a stent with a bioresorbable scaffold comprising a nitric oxide agonist and a polymer comprising a lactide, a glycolide and a lactone, wherein the bioresorbable scaffold exudes the nitric oxide agonist. The nitric oxide agonist may be a statin and the vein is a lower extremity vein.

The present invention also relates to a method for re-endotheliazation in a damaged artery comprising implanting into the damaged artery a stent with a bioresorbable scaffold comprising a nitric oxide agonist and a polymer comprising a lactide, a glycolide and a lactone, wherein the bioresorbable scaffold exudes the nitric oxide agonist. The nitric oxide agonist may be a statin.

The present invention also relates to a method for preventing endothelial dysfunction in a damaged artery comprising implanting into the artery a stent with a bioresorbable scaffold comprising a nitric oxide agonist and a polymer comprising a lactide, a glycolide and a lactone, wherein the bioresorbable scaffold exudes the nitric oxide agonist. The nitric oxide agonist may be a statin.

The present invention also relates to a method for reducing stent thrombosis in a damaged artery comprising implanting into the artery a stent with a bioresorbable scaffold comprising a nitric oxide agonist and a polymer comprising a lactide, a glycolide and a lactone, wherein the bioresorbable scaffold exudes the nitric oxide agonist. The nitric oxide agonist may be a statin. Antiplatelet therapy after stent placement is reduced and bleeding following the stent placement is reduced.

The present invention also relates to a bioresorbable scaffold for a vascular stent comprising a nitric oxide agonist and a polymer selected from the group consisting of polylactide statin, polyglycolide statin, polyepsilon caprolactone statin, polylactide-glycolide-statin, polylactide-epsilon caprolactone-statin, polyglycolide-epsilon caprolactone-statin or mixtures thereof, wherein the amount of statin is in the range from about 1 to about 99 weight percent. The nitric oxide agonist may be a statin or HMG CoA reductase inhibitor. The statin is selected from the group consisting of velostatin, dihydrocompactin, carvastatin, bevastatin, cefvastatin, glenvastatin, simvastatin, lovastatin, atorvastatin, pravastatin, cerivastatin, rosuvastatin, pitavastatin, fluvastatin, mevastatin, dalvastatin, compactin and mixtures thereof. The nitric oxide agonist may be coated on the polymer or may be incorporated within the polymer. The nitric oxide agonist may be chemically bonded to the polymer.

DETAILED DESCRIPTION OF THE INVENTION

Below are definitions for terms related to this invention. In describing and claiming the present invention, the following terminology will be used in accordance with the definitions set out below. Notwithstanding, other terminology and definitions may also be found throughout this disclosure as well.

Bioresorbable—the materials that can be broken down by the body and that do not require removal, such as sutures or the chlorhexidine chip.

Bioresorption—A term indicating a process wherein a bioresorbable polymer is eliminated from the body by dissolution, assimilation, decomposition, or degradation Biodegradable—capable of being broken down especially into innocuous products by the action of living things (such as microorganisms). The antirestenosis drug containing polymers used to coat the outside surface of scaffolds of drug-eluting stents are biodegradable. Once the drug is eluted the polymer carrying the drug is biodegraded Scaffold—the core spring or mesh-like element of a stent which functions mechanically to prop open and maintain a vascular lumen in the open position. In the case of stents which are "bare", and not drug-eluting, the scaffold is in essence the stent itself. Scaffolds have cross member structures arranged like rungs in a ladder that exert force in a vector perpendicular to the vessel wall to maintain the vessel lumen in an open position. These cross member structures are called struts. There is also a strut-free scaffold or scaffold-like device which is V shaped. It is used to stabilize vulnerable plaques in coronary arteries prior to rupture so as to prevent myocardial infarction. This device is called a V-shield™.

Platform—synonymous with scaffold as defined above.

Intrinsic—refers to pharmacologic bioactivity inherent in a molecular structure which is exclusive of the pharmacologic activity of agents located in the vicinity of but acting external to the same molecular structure. Intrinsic activity differs from extrinsic activity. Extrinsic bioactivity refers to pharmacologic activity from molecules that are not chemically bonded within the structure of the polylactide polymer itself.

Regarding the term "bioresorbable" as it applies to a bioresorbable scaffold, the scaffold does not require removal because it is reabsorbed into the surrounding vasculature when it is broken down. The term biodegradable, on the other hand, would only require the scaffold to be broken down by biological processes without specifying the final fate of the products of the decomposition process.

Nitric Oxide Agonists

Unlike nitric oxide donors which release nitric oxide from the donor molecule itself, nitric oxide agonists are agents that increase or upregulate nitric oxide production from the enzyme nitric oxide synthase (NOS). NOS upregulation involves increases in NOS activity or gene expression produced by agents referred to as NOS agonists. Other types of nitric oxide agonists include, but are not limited to, NOS substrate (L-arginine), NOS cofactor (tetrahydrobiopterin—BH4) and L-arginine equivalents. See Kaesemeyer, U.S. Pat. No. 5,767,160. A gene for NOS and related genetic materials can also function as a nitric oxide agonist when it is transfected into the lumenal wall of blood vessels.

NOS agonists can be either physiologic or pharmacologic. Examples of physiologic agonists of NOS include, but are not limited to, acetylcholine, bradykinin, histamine, serotonin and substance P. Pharmacologic NOS agonists include, but are not limited to, inhibitors of converting enzyme or kinase II, angiotensin receptor blockers, endothelin antagonists, certain beta blockers such as nevibilol and HMG CoA reductase inhibitors or statins. NOS agonists, especially statins, have the ability to acutely activate NOS. See Kaesemeyer et al., "Pravastatin Sodium Activates Endothelial Nitric Oxide Synthase Independent of its Cholesterol Lowering Actions," 33:234-41 (1999); and Datar et al., "Acute Activation of eNOS by Statins Involves Scavenger Receptor—B1, G-Protein Subunit Gi Phospholipase C and Calcium Influx," Br J Pharmacol. 160: 1765-1772 (2010). Because of their ability to acutely activate NOS and promote re-endothelialization, in addition to having structures possessing lactone rings, statins are felt to be ideally suited for preventing stent thrombosis. See Kaesemeyer, "Statin DES for Early Stent Thrombosis," Atherosclerosis. 207: 343 (2009). However, it is conceivable that other nitric oxide agonists mentioned above such as L-arginine, BH4, L-arginine equivalents and transfected NOS gene and related genetic materials, could be used alone or modified so as to function as prodrugs containing lactone rings suitable for forming polylactide polymers with nitric oxide enhancing capabilities similar to statins.

Examples of L-arginine equivalents include, but are not limited to, citrulline, arginase inhibitors and the antioxidants n-acetyl-L-cysteine, ascorbic acid, tempol, hydralazine, and pentaerythritol tetranitrate (PETN). Citrulline functions as a prodrug which is converted to L-arginine. Arginase inhibitors block the shunting of L-arginine into the orthnithine cycle and thereby increase the availability of L-arginine to NOS. The antioxidants prevent oxidative injury to the CAT 1 or y+ transporter which provides for the uptake of L-arginine into the endothelial cell and its delivery to NOS which utilizes L-arginine to produce (endothelium derived) nitric oxide.

NOS agonists may contain a lactone ring. The NOS agonists may be incorporated into the polymer as a result of undergoing a ring opening polymerizarion in a similar way as does epsilon-caprolactone.

Statins

There are a number of statins that are available and approved for use. These include, but are not limited to, mevastatin, lovastatin, pravastatin, simvastatin, velostatin, dihydrocompactin, fluvastatin, atorvastatin, dalvastatin, carvastatin, cerivastatin, bevastatin, cefvastatin, rosuvastatin, pitavastatin, compactin, and glenvastatin. Preferred statins are simvastatin, lovastatin, atorvastatin, pravastatin, cerivastatin, rosuvastatin, pitavastatin, fluvastatin, mevastatin, dalvastatin, compactin. The statin compounds are administered in regimens and at dosages known in the art. For example, fluvastatin sodium, marketed by Novartis Pharmaceuticals as Lescol is recommended for a 20-80 mg daily oral dose range, preferably between 20 and 40 mg/day for the majority of patients. 20 to 40 mg daily doses are preferably taken once daily at bedtime. 80 mg daily doses is prescribed as 40 mg doses b.i.d. and recommended only for those individuals in which the 40 mg daily dose is inadequate to lower LDL levels satisfactorily. Atorvastatin, marketed by Pfizer as Lipitor, has a recommended starting daily dose of 10 mg once daily, with an overall daily dose range of from 10 to 80 mg. Simvastatin, marketed by Merck & Co., Inc., may be administered with a starting dose of 20 mg once a day in the evening, or a 10 mg dose per day for those requiring only a moderate reduction in LDL levels. The recommended overall daily dosage range taken as a single evening dose is from 5 to 80 mg. Pravastatin sodium, marketed as Pravachol™ by Bristol-Meyers Squibb, has a recommended starting dose of 10 or 20 mg per day, taken daily as a single dose at bedtime, with a final overall daily range of from 10 to 40 mg. Lovastatin, marketed by Merck & Co. as Mevacor™, has a recommended daily starting dosage of 20 mg per day taken with the evening meal. The recommended final daily dosage range is from 10 to 80 mg per day in single or divided doses. Pitavastatin, the most recently approved drug in this class, is administered in a dose range of between 1-4 mg per day. In general, all of these statins are formulated in a simple delivery system which involves immediate-release kinetic profiles of the statin monomer.

All of the above statins can be made to exist in both closed or open lactone ring forms. In order to form a polylactide polystatin polymer one would want to use a statin with an intact lactone ring such as lovastatin or simvastatin as described below.

Polylactide Terpolymers

The polymers of the present invention comprise L(-) lactide, glycolide, and a lactone.

The method of making L(-) lactide-glycolide-epsilon-caprolactone terpolymers is described by Goldberg, U.S. Pat. No. 5,085,629, whose disclosure is expressly incorporated by reference herein in its entirety.

Generally, the amount of L(-)lactide is in the range of from about 45 to about 85 weight %, preferably about 55 to about 75 weight % and most preferably about 60 to about 70 weight % of the polymer composition.

Generally, the amount of glycolide is in the range of from about 5 to about 50 weight %, and preferably about 10 to 30 weight % of the polymer composition.

Generally the amount of lactone is in the range of from about 15 and about 25% by weight of the polymer composition.

The lactone can be a statin with an intact lactone ring. Statins with an intact lactone ring include lovastatin or simvastatin. The amount of the statin with the intact lactone ring can be up to 100% of the lactone component of the polymer.

A L(-) lactide-glycolide-simvastatin terpolymer (polysimvastatin) is formed in accordance with the method described by Goldberg, U.S. Pat. No. 5,085,629. In the preparation of polysimvastatin, simvastatin substitutes as the lactone ring containing substrate for epsilon caprolactone to form a terpolymer. Thus, in the present invention the scaffold itself is a drug, or more precisely, a prodrug from which a drug is exuded when the scaffold is bioresorbed.

Also, in another embodiment, a nitric oxide agonist can be added to a L(-) lactide-glycolide-simvastatin terpolymer matrix. Thus, the nitric oxide agonist can be co-exuded when the scaffold is bioresorbed. The nitric oxide agonist may be any of those as listed above and preferably can be an L-arginine equivalent or a gene for NOS. BH4 and NOS substrate (L-arginine) can also be used. The nitric oxide agonist serves to potentiate the effect of the statin in the scaffold during the process of bioresorption.

The resulting terpolymer is then extruded into the formation of a scaffold for use in vascular stent construction. The stent may be "bare", i.e. scaffold used alone, or may have drugs applied directly or have a polymer applied to this scaffold which contains drugs for elution which prevent smooth muscle proliferation, neointimal hyperplasia and restenosis. In this later case one would have a stent capable of delivering two drugs—one targeting the endothelium and the risk of stent thrombosis and the other targeting the risk of restenosis—to the site of procedure related vascular lumen injury. This may markedly reduce the requirement for antiplatelet therapy post procedure and the risk of bleeding and death from bleeding. The stent so formed is suitable for use in carotid, intracranial, aorta, subclavian, peripheral, renal and coronary arteries, as well as in veins such as veins of the lower extremities. Preferably, the stent is used in coronary arteries for the treatment of occlusions from atherothrombosclerotic diseases.

Additional Polymers Useful in the Present Invention

In addition to the above described terpolymer, the present invention also provides for the following copolymers and terpolymers incorporating statins:

Polylactide Statin Copolymer.

Generally, the amount of the lactide component may range from about 1 to about 99 weight percent with the amount of the statin component of the copolymer ranging from about 99 to about 1 weight percent. The polylactide statin copolymer does not contain any glycolide or epsilon-caprolactone. For example, the ratio of lactide to statin may fall within the range from about 1:99 weight percent of lactide to statin (1 weight percent of lactide to 99 weight percent statin); about 10:90 weight percent of lactide to statin; about 20:80 weight percent of lactide to statin; about 30:70 weight percent of lactide to statin; about 40:60 weight percent of lactide to statin; about 50:50 weight percent of lactide to statin; about 60:40 weight percent of lactide to statin; about 70:30 weight percent of lactide to statin; about 75:25 weight percent of lactide to statin; about 80:20 weight percent of lactide to statin; about 90:10 weight percent of lactide to statin; and about 99:1 weight percent of lactide to statin.

Polyglycolide Statin Copolymer.

Generally, the amount of glycolide component may range from about 1 to about 99 weight percent with the amount of the statin component of the copolymer ranging from about 99 to about 1 weight percent. The polyglycolide statin copolymer does not contain any lactide or epsilon-caprolactone. For example, the ratio of glycolide to statin may fall within the range from about 1:99 weight percent of glycolide to statin; about 10:90 weight percent of glycolide to statin; about 20:80 weight percent of glycolide to statin; about 30:70 weight percent of glycolide to statin; about 40:60 weight percent of glycolide to statin; about 50:50 weight percent of glycolide to statin; about 60:40 weight percent of glycolide to statin; about 70:30 weight percent of glycolide to statin; about 75:25 weight percent of glycolide to statin; about 80:20 weight percent of glycolide to statin; about 90:10 weight percent of glycolide to statin; and about 99:1 weight percent of glycolide to statin.

Polyepsilon-Caprolactone Statin Copolymer.

Generally, the amount of epsilon-caprolactone component may range from about 1 to about 99 weight percent with the amount of the statin component of the copolymer ranging from about 99 to about 1 weight percent. The polyepsiloncaprolactone statin copolymer does not contain any lactide or glycolide. For example, the ratio of epsilon-caprolactone to statin may fall within the range from about 1:99 weight percent of epsilon-caprolactone to statin; about 10:90 weight percent of epsilon-caprolactone to statin; about 20:80 weight percent of epsilon-caprolactone to statin; about 30:70 weight percent of epsilon-caprolactone to statin; about 40:60 weight percent of epsilon-caprolactone to statin; about 50:50 weight percent of epsilon-caprolactone to statin; about 60:40 weight percent of epsilon-caprolactone to statin; about 70:30 weight percent of epsilon-caprolactone to statin; about 75:25 weight percent of epsilon-caprolactone to statin; about 80:20 weight percent of epsilon-caprolactone to statin; about 90:10 weight percent of epsilon-caprolactone to statin; and about 99:1 weight percent of epsilon-caprolactone to statin.

Polylactide Glycolide Statin Terpolymer.

Generally, the amount of lactide and glycolide component may range from about 1 to about 99 weight percent with the amount of the statin component of the terpolymer ranging from about 99 to about 1 weight percent. The polylactide glycolide statin terpolymer does not contain any epsilon-caprolactone. For example, the ratio of the lactide and glycolide component to statin may fall within the range from about 1:99 weight percent of the lactide and glycolide component to statin; about 10:90 weight percent of lactide and glycolide component to statin; about 20:80 weight percent of lactide and glycolide component to statin; about 30:70 weight percent of lactide and glycolide component to statin; about 40:60 weight percent of lactide and glycolide component to statin; about 50:50 weight percent of lactide and glycolide component to statin; about 60:40 weight percent of lactide and glycolide component to statin; about 70:30 weight percent of lactide and glycolide component to statin; about 80:20 weight percent of lactide and glycolide component to statin; about 85:15 weight percent of lactide and glycolide component to statin; about 90:10 weight percent of lactide and glycolide component to statin; and about 99:1 weight percent of lactide and glycolide component to statin.

With respect to the lactide and the glycolide component of the terpolymer, the amount of lactide may range from about 1 to about 99 weight percent with the amount of glycolide ranging from about 99 to about 1 weight percent. For example, the ratio of lactide to glycolide may fall within the range from about 1:99 weight percent of lactide to glycolide; about 10:90 weight percent of lactide to glycolide; about 20:80 weight percent of lactide to glycolide; about 30:70 weight percent of lactide to glycolide; about 40:60 weight percent of lactide to glycolide; about 50:50 weight percent of lactide to glycolide; about 60:40 weight percent of lactide to glycolide; about 70:30 weight percent of lactide to glycolide; about 75:25 weight percent of lactide to glycolide; about 80:20 weight percent of lactide to glycolide; about 90 weight percent of lactide to glycolide; and about 99:1 weight percent of lactide to glycolide.

A preferred polylactide glycolide statin terpolymer comprises 70 weight percent lactide, 15 weight percent glycolide and 15 weight percent statin in the absence of any epsilon-caprolactone.

Polylactide Epsilon-Caprolactone Statin Terpolymer.

Generally, the amount of the lactide and epsilon-caprolactone component may range from about 1 to about 99 weight percent with the amount of the statin ranging from about 99 to about 1 weight percent. The polylactide epsilon-caprolactone statin terpolymer does not contain any glycolide. For example, the ratio of lactide and epsilon-caprolactone component to statin may fall within the range from about 1:99 weight percent of lactide and epsilon-caprolactone component to statin; about 10:90 weight percent of lactide and epsilon-caprolactone component to statin; about 20:80 weight percent of lactide and epsilon-caprolactone component to statin; about 30:70 weight percent of lactide and epsilon-caprolactone component to statin; about 40:60 weight percent of lactide and epsilon-caprolactone component to statin; about 50:50 weight percent of lactide and epsilon-caprolactone component to statin; about 60:40 weight percent of lactide and epsilon-caprolactone component to statin; about 70:30 weight percent of lactide and epsilon-caprolactone component to statin; about 80:20 weight percent of lactide and epsilon-caprolactone component to statin; about 85:15 weight percent of lactide and epsilon-caprolactone component to statin; about 90:10 weight percent of lactide and epsilon-caprolactone component to statin; and about 99:1 weight percent of lactide and epsilon-caprolactone component to statin.

With respect to the lactide and epsilon-caprolactone component of the terpolymer, the amount of lactide may range from about 1 to about 99 weight percent with the epsilon-caprolactone ranging from about 99 to about 1 weight percent. For example, the ratio of lactide to epsilon-caprolactone may fall within the range from about 1:99 weight percent of lactide to epsilon-caprolactone; about 10:90 weight percent of lactide to epsilon-caprolactone; about 20:80 weight percent of lactide to epsilon-caprolactone; about 30:70 weight percent of lactide to epsilon-caprolactone; about 40:60 weight percent of lactide to epsilon-caprolactone; about 50:50 weight percent of lactide to epsilon-caprolactone; about 60:40 weight percent of lactide to epsilon-caprolactone; about 70:30 weight percent of lactide to epsilon-caprolactone; about 75:25 weight percent of lactide to epsilon-caprolactone; about 80:20 weight percent of lactide to epsilon-caprolactone; about 90:10 weight percent of lactide to epsilon-caprolactone; and about 99:1 weight percent of lactide to epsilon-caprolactone.

A preferred lactide epsilon-caprolactone-statin terpolymer comprises 70 weight percent lactide, 15 weight percent epsilon-caprolactone and 15 weight percent statin in the absence of any glycolide.

Polyglycolide Epsilon-Caprolactone Statin Terpolymer.

Generally, the amount of glycolide and epsilon-caprolactone component ranges from about 1 to about 99 weight percent with the statin component of the terpolymer ranging from about 99 to about 1 weight percent. The polyglycolide epsilon-caprolactone statin terpolymer does not contain any lactide. For example, the ratio of glycolide to epsilon-caprolactone may fall within the range from about 1:99 weight percent of glycolide and epsilon-caprolactone component to statin; about 10:90 weight percent of glycolide and epsilon-caprolactone component to statin; about 20:80 weight percent of glycolide and epsilon-caprolactone component to statin; about 30:70 weight percent of glycolide and epsilon-caprolactone component to statin; about 40:60 weight percent of glycolide and caprolactone component to statin; about 50:50 weight percent of glycolide and caprolactone component to statin; about 60:40 weight percent of glycolide and epsilon-caprolactone component to statin; about 70:30 weight percent of glycolide and epsilon-caprolactone component to statin; about 80:20 weight percent of glycolide and epsilon-caprolactone component to statin; about 85:15 weight percent of glycolide and epsilon-caprolactone component to statin; about 90:10 weight percent of glycolide and epsilon-caprolactone component to statin; and about 99:1 weight percent of glycolide and epsilon-caprolactone component to statin.

With respect to the glycolide and epsilon-caprolactone component of the glycolide epsilon-caprolactone statin terpolymer, the amount of glycolide may range from about 1 to about 99 weight percent with the epsilon-caprolactone ranging from about 99 to about 1 weight percent. For example, the ratio of glycolide to epsilon-caprolactone may fall within the range from about 1 weight percent of glycolide to 99 weight percent of epsilon-caprolactone; about 10:90 weight percent of glycolide to epsilon-caprolactone; about 20:80 weight percent of glycolide to epsilon-caprolactone; about 30:70 weight percent of glycolide to epsilon-caprolactone; about 40:60 weight percent of glycolide to epsilon-caprolactone; about 50:50 weight percent of glycolide to epsilon-caprolactone; about 60:40 weight percent of glycolide to epsilon-caprolactone; about 70:30 weight percent of glycolide to epsilon-caprolactone; about 75:25 weight percent of glycolide to epsilon-caprolactone; about 80:20 weight percent of glycolide to epsilon-caprolactone; about 90:10 weight percent of glycolide to epsilon-caprolactone; and about 99:1 glycolide to epsilon-caprolactone.

A preferred polyglycolide epsilon-caprolactone statin terpolymer comprises 70 weight percent glycolide, 15 weight percent epsilon-caprolactone and 15 weight percent statin.

Finally, it should be noted that oral statin dosing as described above will not be changed by this invention. Statins delivered locally by this scaffold will be resorbed by the vessel wall and will not have systemic effects. Vulnerable plaques are distributed throughout the coronary artery tree and the ones that are most prone to rupture and cause initial thrombus formation are the ones in arteries that are minimally narrowed. These lesions are generally not candidates for stenting. For these lesions oral systemic statin therapy is crucial. But for those lesions that are stentable, statins delivered locally at the site of the injury produced by the procedure are needed to promote endothelial regrowth and to offset the effect of drugs eluted from polymers coated onto the surface of scaffolds that prevent restenosis but cause endothelial dysfunction, inhibit re-endothelialization, increase the risk of stent thrombosis and prolong the requirement for dual antiplatelet therapy and risk of bleeding following stent placement.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

What is claimed is:

1. A vascular stent comprising a bioresorbable scaffold comprising a polymer wherein the polymer comprises statin and one or more monomers selected from the group consisting of lactide, glycolide, and epsilon-caprolactone wherein the statin is incorporated as repeating monomeric units into the body of the polymer.

2. The vascular stent of claim 1, wherein the statin is selected from the group consisting of velostatin, dihydrocompactin, carvastatin, bevastatin, cefvastatin, glenvastatin, simvastatin, lovastatin, atorvastatin, pravastatin, cerivastatin, rosuvastatin, pitavastatin, fluvastatin, mevastatin, dalvastatin, compactin and mixtures thereof.

3. The vascular stent of claim 2, wherein the statin is selected from the group consisting of simvastatin, lovastatin, atorvastatin, pravastatin, cerivastatin, rosuvastatin, pitavastatin, fluvastatin, mevastatin, dalvastatin, and compactin.

4. The vascular stent of claim 1, wherein the polymer is selected from the group consisting of polylactide statin, polyglycolide statin, polyepsilon caprolactone statin, polylactide-glycolide statin, polylactide-epsilon caprolactone statin, polyglycolide-epsilon caprolactone statin, polylactide glycolide-epsilon-caprolactone statin and mixtures thereof.

5. The vascular stent of claim 4, wherein the statin is selected from the group consisting of velostatin, dihydrocompactin, carvastatin, bevastatin, cefvastatin, glenvastatin, simvastatin, lovastatin, atorvastatin, pravastatin, cerivastatin, rosuvastatin, pitavastatin, fluvastatin, mevastatin, dalvastatin, compactin and mixtures thereof.

6. The vascular stent of claim 5, wherein the statin is selected from the group consisting of simvastatin, lovastatin, atorvastatin, pravastatin, cerivastatin, rosuvastatin, pitavastatin, fluvastatin, mevastatin, dalvastatin, and compactin.

7. The vascular stent of claim 4, wherein the polymer is polylactide statin.

8. The vascular stent of claim 7, wherein the statin is selected from the group consisting of velostatin, dihydrocompactin, carvastatin, bevastatin, cefvastatin, glenvastatin, simvastatin, lovastatin, atorvastatin, pravastatin, cerivastatin, rosuvastatin, pitavastatin, fluvastatin, mevastatin, dalvastatin, compactin and mixtures thereof.

9. The vascular stent of claim 8, wherein the statin is selected from the group consisting of simvastatin, lovastatin, atorvastatin, pravastatin, cerivastatin, rosuvastatin, pitavastatin, fluvastatin, mevastatin, dalvastatin, and compactin.

10. The vascular stent of claim 4, wherein the polymer is polyglycolide statin.

11. The vascular stent of claim 10, wherein the statin is selected from the group consisting of velostatin, dihydrocompactin, carvastatin, bevastatin, cefvastatin, glenvastatin, simvastatin, lovastatin, atorvastatin, pravastatin, cerivastatin, rosuvastatin, pitavastatin, fluvastatin, mevastatin, dalvastatin, compactin and mixtures thereof.

12. The vascular stent of claim 11, wherein the statin is selected from the group consisting of simvastatin, lovastatin, atorvastatin, pravastatin, cerivastatin, rosuvastatin, pitavastatin, fluvastatin, mevastatin, dalvastatin, and compactin.

13. The vascular stent of claim 4, wherein the polymer is polyepsilon caprolactone statin.

14. The vascular stent of claim 13, wherein the statin is selected from the group consisting of velostatin, dihydrocompactin, carvastatin, bevastatin, cefvastatin, glenvastatin, simvastatin, lovastatin, atorvastatin, pravastatin, cerivastatin, rosuvastatin, pitavastatin, fluvastatin, mevastatin, dalvastatin, compactin and mixtures thereof.

15. The vascular stent of claim 14, wherein the statin is selected from the group consisting of simvastatin, lovastatin, atorvastatin, pravastatin, cerivastatin, rosuvastatin, pitavastatin, fluvastatin, mevastatin, dalvastatin, and compactin.

16. The vascular stent of claim 4, wherein the polymer is polylactide glycolide statin.

17. The vascular stent of claim 16, wherein the statin is selected from the group consisting of velostatin, dihydrocompactin, carvastatin, bevastatin, cefvastatin, glenvastatin, simvastatin, lovastatin, atorvastatin, pravastatin, cerivastatin, rosuvastatin, pitavastatin, fluvastatin, mevastatin, dalvastatin, compactin and mixtures thereof.

18. The vascular stent of claim 17, wherein the statin is selected from the group consisting of simvastatin, lovastatin, atorvastatin, pravastatin, cerivastatin, rosuvastatin, pitavastatin, fluvastatin, mevastatin, dalvastatin, and compactin.

19. The vascular stent of claim 4, wherein the polymer is polylactide epsilon caprolactone statin.

20. The vascular stent of claim 19, wherein the statin is selected from the group consisting of velostatin, dihydrocompactin, carvastatin, bevastatin, cefvastatin, glenvastatin, simvastatin, lovastatin, atorvastatin, pravastatin, cerivastatin, rosuvastatin, pitavastatin, fluvastatin, mevastatin, dalvastatin, compactin and mixtures thereof.

21. The vascular stent of claim 20, wherein the statin is selected from the group consisting of simvastatin, lovastatin, atorvastatin, pravastatin, cerivastatin, rosuvastatin, pitavastatin, fluvastatin, mevastatin, dalvastatin, and compactin.

22. The vascular stent of claim 4, wherein the polymer is polyglycolide epsilon caprolactone statin.

23. The vascular stent of claim 22, wherein the statin is selected from the group consisting of velostatin, dihydrocompactin, carvastatin, bevastatin, cefvastatin, glenvastatin, simvastatin, lovastatin, atorvastatin, pravastatin, cerivastatin, rosuvastatin, pitavastatin, fluvastatin, mevastatin, dalvastatin, compactin and mixtures thereof.

24. The vascular stent of claim 23, wherein the statin is selected from the group consisting of simvastatin, lovastatin, atorvastatin, pravastatin, cerivastatin, rosuvastatin, pitavastatin, fluvastatin, mevastatin, dalvastatin, and compactin.

25. The vascular stent of claim 4, wherein the polymer is polylactide glycolide-epsilon-caprolactone statin.

26. The vascular stent of claim 25, wherein the statin is selected from the group consisting of velostatin, dihydrocompactin, carvastatin, bevastatin, cefvastatin, glenvastatin, simvastatin, lovastatin, atorvastatin, pravastatin, cerivastatin, rosuvastatin, pitavastatin, fluvastatin, mevastatin, dalvastatin, compactin and mixtures thereof.

27. The vascular stent of claim 26, wherein the statin is selected from the group consisting of simvastatin, lovastatin, atorvastatin, pravastatin, cerivastatin, rosuvastatin, pitavastatin, fluvastatin, mevastatin, dalvastatin, and compactin.

\* \* \* \* \*